United States Patent [19]

Korshak et al.

[11] 4,009,044
[45] Feb. 22, 1977

[54] ADHESIVE COMPOSITION

[76] Inventors: Vasily Vladimirovich Korshak, ulitsa Gubkina, 4, kv. 81; Antonina Mikhailovna Polyakova, ulitsa Vavilova, 55/7, kv. 54; Kira Alexandrovna Mager, Beskudnikovsky bulvar, 10, korpus 11, kv. 44; Vyacheslav Nikolaevich Semyantsev, ulitsa Gorkogo, 28, kv. 6, all of Moscow, U.S.S.R.

[22] Filed: Mar. 7, 1975

[21] Appl. No.: 556,538

[52] U.S. Cl. .............................. 106/287 R; 526/281
[51] Int. Cl.$^2$ ................................................ C09K 3/00
[58] Field of Search ............... 106/287; 260/465.9, 260/465.4, 78.5 N, 78.4 N, 89.5 H, 881; 526/298

[56]  References Cited
UNITED STATES PATENTS

| 2,642,416 | 6/1953  | Ahlbrecht ............... 260/89.5 H |
| 2,763,585 | 9/1956  | Coover et al. ............ 260/78.5 N |
| 2,816,093 | 12/1957 | Coover ..................... 260/881 |
| 3,759,264 | 9/1973  | Coover, Jr. et al. ............ 526/298 |

OTHER PUBLICATIONS

"The Tensile Strength of Adhesive Joints Between Eye Tissue and Alloplastic Materials," RE FOJO, M. F. et al., American Jour. of Ophthalmology, vol. 68, No. 2, pp. 248-255, 1968, Aug.

Primary Examiner—Theodore Morris
Attorney, Agent, or Firm—Haseltine, Lake & Waters

[57] ABSTRACT

An adhesive composition containing monomeric α-cyan acrylates - alkyl -α-cyan acrylates having from 1 to 7 carbon atoms, and/or allyl-α-cyan acrylate, as well as a modifying additive comprising fluorinated methacrylate or fluorinated acrylate of the general formula

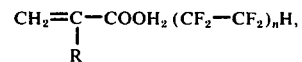

wherein $n=1-3$, R is H, $CH_3$, or $CH_2-C-\ COOH_2 (CF_2)_{n_1} CF_3$, wherein $n_1=1-2$ and R has the abovementioned significances. Monomeric α-cyan acrylates are used in an amount of 70–90 w.% and the modifying additive in an amount of 10–30 w.%.

A strength of adhesive bond obtained using the adhesive compositions according to the invention attains 180–190 kp/cm². The adhesive bond exhibits a considerable flexibility and hydrolytic stability.

4 Claims, No Drawings

ADHESIVE COMPOSITION

The present invention relates to adhesive compositions, and more specifically to instantaneous action adhesive compositions on the basis of monomeric α-cyan acrylates of the general formula CH₂=C (CN) — COOR, wherein R is alkyl having from 1 to 60 carbon atoms, alkenyl, phenyl, cyclohexyl, alkoxyalkyl and the like.

These adhesive compositions (adhesives) find a wide application in diverse fields of technology: in mechanical engineering, instrumentation, electronic, mining and aircraft industries, in the manufacture of time pieces and in jewelery. These adhesives are also used in the medicine, especially in surgery for seamless interconnection of tissues of a living body.

These adhesives are of a versatile character. They are capable of bonding practically all materails including glass, metals, wood, diverse plastics, etc. No catalysts, heating or pressure application are required for curing of these adhesives. They are cured under the action of moisture traces available on the surfaces being treated and in the environment. The absence of any solvent in the adhesive composition eliminates the need of exposing the surfaces being bonded in the air for removing a solvent prior to their interconnection. The adhesive sets instantaneously after the interconnection of the mating surfaces to obtain a strong adhesive bond.

The above-described α-cyan acrylate adhesives may contain various modifying additives, such as plasticizers, viscosity controllers and the like.

In addition, the adhesive composition may contain an inhibitor of radical polymerization, such as hydroquinone, methylhydroquinone and the like. The adhesives of this type may also contain mixtures of different monomeric cyan acrylates.

Known in the art are adhesive compositions containing, in addition to monomeric α-cyan, acrylates, other monomers as modifying additives. Thus, it is known to use a composite adhesive containing a monomeric ester of α-cayn acrylic acid, wherein ester roup is represented by alkyl having from 1 to 8 carbon atoms, alkenyl, cyclohexyl and phenyl and a modifying additive, such as vinyl-aromatic monomer, e.g. styrene, α-methylstyrene and other styrene derivatives in at least equimolar amont against cyan acrylate.

The use of such monomers in the composition of cyan acrylate adhesive provides for a higher strength and water resistance of the adhesive bond.

This adhesive composition (adhesive) has, however, an insufficient stability. Its life is generally from 10 to 30 minutes. This is due to the fact that upon mixing the above-mentioned components, that is α-cyan acrylate and vinyl-aromatic monoriers, a apid polymerization occurs. This results in the need of adding vinyl-aromatic monomer to the composition directly prior the cementation, or applying one of the components to one surface being treated, and the other component to the other surface with subsequent interconnection of these surfaces. This complicates the employment of the adhesive and limits the field of its application.

It is also known to use an adhesive composition containing monomeric α-cyan acrylates, such as ethyl- α-cyan acrylate, and a modifying additive, such as vinylacetylene monomer - dimethylvinyl ethynylcarbinol and its derivatives in an amount from 5 to 30% by weight of the composition.

The use of these monomers provides for a sufficient strength and flexibility of the adhesive bond, but with a high content of said modifying additive, of the order of 30% and more, the strength of the adhesive bond is reduced inspite of a better flexibility thereof.

It is also known to use cyan acrylate adhesive compositions containing monomeric acrylates.

Thus, one prior art composition comprises a mixture of monomeric alkyl-α-cyan acrylate with 1 to 4 carbon atoms in alkyl group used in an amount for at least 50 w.%, 1–49 w.% of monomeric alkyl acrylate with from 1 to 4 carbon atoms in alkyl group and 1–15 w.% of bifunctional monomer used as cross-linking agent, such as allyl acrylate or divinyl benzene.

The combination of monomeric α-cyan acrylates with acrylates was aimed at the cost reduction of adhesive cyan-acrylate compositions and making them more available.

Polymerization of such composition occurs in two stages. First, alkyl- α-cyan acrylate is rapidly polymerized to ensure the setting together of the parts being cemented, and then acrylates are polymerized during a comparatively long time period (several days). As a result, a strong adhesive bond is obtained.

In order to accelerate the second stage of polymerization, it is necessary to add an initiator of polymerization, such as acetyl peroxide.

The use of a promoter of polymerization complicates the cementing process since the peroxide should be added directly before the cementing. The use of the peroxide itself is unsafe because the peroxide is explosion hazardous. It should be noted that the storage of the adhesive composition in a mixture with the promoter is absolutely impossible since it would result in a premature uncontrolled polymerization of the components of adhesive composition.

As to the mechanical properties of the adhesive bond obtained when using such adhesive composition, no data have been reported on the strength and flexibility. Laboratory tests conducted with an adhesive bond obtained with the employment of this adhesive composition to determine the strength and flexibility thereof have shown that the strength of the adhesive bond was rather low. Thus, in cementing together plates of duralumin, the strength of bond was 90–130 kp/cm².

It is an object of the invention to provide an adhesive composition which ensures an adhesive bond exhibiting elevated physical and mechanical characteristics while having a sufficient stability.

With this and other objects in view, the invention consists in the provision of an adhesive composition containing monomeric α-cyan acrylates - alkyl- α-cyan acrylates, wherein alkyl group has from 1 to 7 carbon atoms, and/or allyl- α-cyan acrylate, as well as a modifying additive. In accordance with the invention, the modifying additive used in the adhesive composition comprises fluorinated methacrylate or fluorinated acrylate of the general formula $$CH_2=C-COOCH_2(CF_2-CF_2)_n H,$$
$$|$$
$$R$$

wherein n=1–3, R is H, CH₃ or

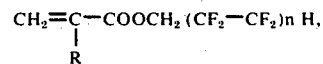

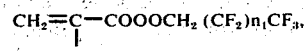

above-mentioned significances, monomeric α-cyan acrylates being used in an amount of 70–90 w.% and the modifying additive in an amount of 10–30 w.%.

Along with fluorinated methacrylates and acrylates, also the respective monomers may be used with n greater than 3 and with $n_1$ greater than 2, but these substances are difficultly available.

The addition of 10–30 w.% of fluorinated monomer is an optimum one: smaller amounts are rather ineffective, and greater amounts of the additive will result in a lower strength of the adhesive bond.

In order to improve the stability of the adhesive composition, an inhibitor of radical polymerization is prefereably added thereto in an amount of 0.01–0.05% by weight of the composition.

The inhibitor of radical polymerization may comprise hydroquinone or methylhydroquinone.

The addition of fluorinated methacrylates or fluorinated acrylates to the adhesive composition considerably improves physical and mechanical properties of the adhesive bond.

It is known that the strength of an adhesive bond may attain a considerable value where the surface tension of the adhesive composition is smaller than the surface tension value of the surface being cemented (cl. L. Dimiter, Klebstoffe fur Plaste, Leipzig, 1966, pp. 59–61).

It is also known that the substitution of fluorine for hydrogen in compounds results in a reduced surface tension (cf. Manual on Chemistry of Polymers, Naukova Dumka Publishers Kiev, 1971, p. 279). However, the measurements of surface tension of fluorinated methacrylates, fluorinated acrylates and the respective monomers comtaining no fluorine have shown that the values of surface tension vary only slightly. This also applies to the adhesive compositions containing these compounds. Thus, the value of surface tension for 1,1,7-trihydrododecafluoro-n-heptyl methacrylate is 23.000 dyne.cm, and for n-heptyl methacrylates -24 dyne.cm. The values of surface tension for adhesive compositions containing a fluorinated monomer and adhesive composition containing a corresponding monomer without fluorine are given below.

| Adhesive composition | Surface tension (dyne.cm) |
| --- | --- |
| 90 g of ethyl-α-cyan acrylate 10 g of 1,1,5-trihydroocta-fluoro-n-amyl methacrylate | 31.59 |
| 90 g of ethyl-α-cyan acrylate 10 g of n-amyl methacrylate | 31.91 |
| 80 g of ethyl-α-cyan acrylate 20 g of 1,1,5-trihydroocta-fluoro-n-amyl methacrylate | 30.13 |
| 80 g of ethyl-α-cyan acrylate 20 g of n-amyl methacrylate | 30.94 |

Therefore, on the basis of the above, one could expect that such a negligible difference in values of surface tension could not considerably affect the value of strength of an adhesive bond obtained when using the adhesive composition according to the invention, It has been however, surprisingly found that the strength of an adhesive bond obtained when using the adhesive composition containing fluorinated methacrylate or fluorinated acrylate is considerably greater compared to corresponding adhesive compositions containing non-fluorinated monomers. Thus, the strength of adhesive bond obtained using the composition containing 70 w.% of ethyl- α-cyan acrylate and 30 w.% of 1,1,5-thihydrooctafluoro-n-amyl methacrylate was 160 kp/cm², whereas the strength of bond obtained using the composition containing 70 w.% of ethyl- α-cyan acrylate and 30 w.% of methacrylate was only 90 kp/cm².

Shear strength of adhesive bond obtained using the adhesive composition according to the invention when tested at 20° C with duralumine plates of a size 60×20×2 mm as measured 24 hours after cementation was of the order of 180–190 kp/cm².

The adhesive bond thus obtained exhibited a considerable flexibility and hydrolytic stability. Thus, after the exposure in water for 10 days the strength of the adhesive bond was 110–150 kp/cm² with the initial strength of 125–190 kp/cm².

The adhesive composition does not require the use of an inhibitor of radical polymerization.

The adhesive composition according to the invention exhibits a low toxicity and is well compatible with living tissues so that it can be employed in the medicine for cementing living tissues of a body.

In an experiment with 212 rats (observation period from 2 hours to 11 months) the strength of cementation of liver tissues interconnected using the adhesive composition according to the invention was tested.

The reaction of tissues of the action of the adhesive composition and the effects thereof on the wound healing were also studied. In control groups (21 animals) the adhesive was applied in the form of a thin uniform layer to the surface of Glisson's capsule of intact liver.

The hystological study has shown that during the first two days a slight inflamatory reaction occurs in the zone of application of the adhesive which is manifested by hyperaemia and a small oedema. By the end of third-fourth week the simptoms of reactive inflammation completely disappeared. Concurrently, the resorption and redistribution of the adhesive were observed which were characterized by proliferation of cells of granulations around the particles of adhesive with the presence of macrofagi, but without the formation of giant foreign bodies among them. This shows a rapid resorption of the adhesive which is completed by the fourth month. In the zone of application of the adhesive only a slight thickening of serous cover remained due to a thin stratum of fibrous tissue thus formed.

In 181 tests, the adhesive was applied to the surface of a linear wound of a length from 1.5 to 2 mm made by a scalpel through the entire thickness of the organ.

The hystological study has shown that the application of the adhesive introduced no changes into the course and morphology of the wound process, it did not delay the healing of wound and recovery of liver parenchyma in the zone of injury. As early as 2–6 days after, a thin stratum of connective tissue was detected between the wound surfaces which contained minor inclusions of adhesive which penetrated the wound from the surface of the organ. By the end of the first month these inclusions were completely resorbed. The layer of adhesive on the surface of the organ covering the wound underwent the same changes and in the same time as in the control tests with the formation of local fibrous thickening of the capsule.

By the end of the fourth month a delicate connective tissue formed in the wound could not be detected and only small circular-cell infiltrates with a few macrophagi were observed. Single large-size recovering haepatocides were also located in this zone. By the seventh-eleventh months the structure of the liver tissue at the place of the wound became normal.

The adhesive composition according to the invention is stable. It can be stored for a long time (at least 1 year at +5° C).

Unlike the case of fluorocyanacrylate, the method of producing fluorinated acrylates and fluorinated methacrylates is not difficult. These products are obtained at a high yield. For their synthesis readily available products, such as acrylates, methacrylates and fluorinated alcohols are used.

The production method for the preparation of the adhesive composition according to the invention is very simple and may be carried out as follows.

Monomeric α-cyan acrylate containing a stabilizer, which generally comprises sulphur dioxide, is mixed with fluorinated acrylate or fluorinated methacrylate in a polyethylene flask in a flow of dry inert gas. An inhibitor of radical polymerization may be added either to the starting monomeric α-cyan acrylate or to the finished composition.

In some cases, e.g. in cementing porous surfaces, more viscous adhesive composition are preferable. For that purpose, the starting components are mixed in a quartz vessel in a flow of dry inert gas. After the mixing, the resulting adhesive composition is partially polymerized by exposing to UV radiation. The irradiation is effected using, e.g. a quartz mercury-filled lamp of 1000 W capacity at a distance of 30 cm from the radiation source under cooling with running water. Then an inhibitor of radical polymerization, such as hydroquinone or methylhydroquinone is added to the adhesive composition.

The invention will be better understood from the following specific examples.

EXAMPLE 1

80 g of ethyl-α-cyan acrylate and 20 g of 1,1,3-trihydrotetrafluoropropyl methacrylate were mixed in an atmosphere of dry inert gas in a polyethylene flask. The resulting composition was used to cement together plates of duralumin (60×20×2 mm). Shear strength at 20° C 24 hours after the cementation was 150 kp/cm². Elasticity modulus of the cured adhesive composition was 7000 kp/cm².

Shear strength with the above-described plates was tested on a rupture testing machine with the rate of movement of the loading clamp of the machine of 10 mm per minute.

The elasticity modulus was determined by the inclination angle of th first (straight) line of the tension diagram obtained with the compression rate of $1.87.10^{-2}$ mm/s with cylindrical samples of cured adhesive composition of 3 mm diameter and a high of 4.5 mm.

EXAMPLE 2

80 g of ethyl-α-cyan acrylate and 20 g of 1,1,5-trihydrooctafluoro-n-amyl methacrylate were mixed in an atmosphere of dry inert gas in a quartz vessel. The resulting composition was exposed to UV radiation from a quartz mercury-filled lamp of 1000 W at a distance of 30 cm from the radiation source for two hours under cooling of the vessel with running water.

Then 0.05 g of hydroquinone were added to the composition. The kinematic viscosity was 15 cSt at 20° C. Shear strength as measured similarly to that described in Example 1 was 180kp/cm². After the exposure in water at 20° C for 10 days, the shear strength was 145 kp/cm².

EXAMPLE 3

80 g of allyl-α-cyan acrylate containing 0.008 g of methylhydroquinone were mixed with 20 g of 1,1,5-trihydrooctafluoro-n-amyl methacrylate in an atmosphere of dry inert gas in a polyethylene flask. Shear strength as measured similarly to that described in Example 1 was 130 kp/cm². Elasticity modulus of the cured adhesive composition was 6000 kp/cm².

EXAMPLE 4

An adhesive composition was prepared using 80 g of ethyl-α-cyan acrylate and 1,1,5-trihydrooctafluoro-n-amyl acrylate. The preparation of the adhesive composition and testing thereof were conducted as described in Example 1. Shear strength was 150 kp/cm². Elasticity modulus of cured composition was 7000 kp/cm².

EXAMPLE 5

An adhesive composition was prepared using 90 g of ethyl-α-cyan acrylate and 10 g of 1,1,5-trihydrooctafluoro-n-amyl acrylate. The preparation of adhesive composition and testing thereof were conducted as described in Example 1. Shear strength was 150 kp/cm². Elasticity modulus of cured adhesive composition was 9000 kp/cm².

EXAMPLE 6

An adhesive composition was prepared using 80 g of ethyl-α-cyan acrylate and 20 g of 1,1,7-trihydrododecafluoro-n-heptyl acrylate.

The preparation of the composition was conducted as described in Example 2. The composition was tested as described in Example 1. Shear strength was 175 kp/cm². Elasticity modulus of cured composition was 6000 kp/cm².

EXAMPLE 7

An adhesive composition was prepared using 90 g of ethyl-α-cyan acrylate and 10 g of 1,1,3-trihydrotetrafluoro-n-propyl acrylate. The preparation of composition and its testing were conducted as described in Example 1. Shear strength was 125 kp/cm². Elasticity modulus of cured composition was 10000 kp/cm².

EXAMPLE 8

An adhesive composition was prepared using 80 g of ethyl-α-cyan acrylate and 20 g of 1,1-dihydroperfluoro-n-butyl acrylate. The preparation of adhesive composition was conducted as described in Example 2. The adhesive composition was tested as described in Example 1. Shear strength was 150 kp/cm². Elasticity modulus of cured composition was 7000 kp/cm².

EXAMPLE 9

An adhesive composition was prepared using 80 g of ethyl-α-cyan acrylate and 20 g of 1,1-dihydroperfluoro-n-propyl acrylate. The preparation of the composition was conducted as described in Example 2. The adhesive composition was tested as described in Example 1. Shear strength was 140 kp/cm². Elasticity modulus of cured composition was 8000 kp/cm².

EXAMPLE 10

An adhesive composition was prepared using 90 g of ethyl-α-cyan acrylate and 10 g of 1,1,3-trihydrotetrafluoro-n-propyl methacrylate. The preparation and testing of the adhesive composition were conducted as described in Example 1. Shear strength was 130 kp/cm². Elasticity modulus of cured adhesive composition was 1000 kp/cm².

EXAMPLE 11

An adhesive composition was prepared using 90 g of ethyl-α-cyan acrylate and 10 g of 1,1,7-trihydrododecafluoro-n-heptyl methacrylate. The preparation of the adhesive composition was conducted as described in Example 2. The adhesive composition was tested as described in Example 1. Shear strength was 160 kp/cm². Elasticity modulus of cured composition was 9000 kp/cm².

EXAMPLE 12

An adhesive composition was prepared using 80 g of ethyl-α-cyan acrylate and 20 g of 1,1,7-trihydrododecafluoro-n-heptyl methacrylate. The adhesive composition was prepared as described in Example 2. The adhesive composition was tested as described in Example 1. Shear strength was 190 kp/cm². Elasticity modulus of cured adhesive composition was 7000 kp/cm².

EXAMPLE 13

An adhesive composition was prepared using 70 g of ethyl-α-cyan acrylate and 30 g of 1,1,7-trihydrododecafluoro-n-heptyl methacrylate. The preparation of adhesive composition was conducted as described in Example 2. The adhesive composition was tested as described in Example 1. Shear strength was 180 kp/cm². Elasticity modulus of cured adhesive composition was 4700 kp/cm².

EXAMPLE 14

An adhesive composition was prepared using 80 g of n-butyl-α-cyan acrylate and 20 g of 1,1,7-trihydrododecafluoro-n-heptyl methacrylate. The adhesive composition was prepared as described in Example 2. The adhesive composition was tested as described in Example 1. Shear strength was 145 kp/cm². Elasticity modulus of cured adhesive composition was 5000 kp/cm².

EXAMPLE 15

An adhesive composition was prepared using 70 g of n-propyl-α-cyan acrylate and 30 g of 1,1,7-trihydrododecafluoro-n-heptyl methacrylate. The preparation of adhesive composition and its testing were conducted as described in Example 1. Shear strength was 140 kp/cm². Elasticity modulus of cured adhesive composition was 4000 kp/cm².

EXAMPLE 16

An adhesive composition was prepared using 80 g of n-amyl-α-cyan acrylate and 20 g of 1,1,5-trihydrooctafluoro-n-amyl methacrylate. The preparation and testing of adhesive composition were conducted as described in Example 1. Shear strength was 130 kp/cm². Elasticity modulus of cured adhesive composition was 4000 kp/cm².

EXAMPLE 17

An adhesive composition was prepared using 80 g of n-amyl-α-cyan acrylate and 20 g of 1,1-dihydroperfluoro-n-butyl methacrylate. The preparation and testing of adhesive composition were conducted as described in Example 1. Shear strength was 140 kp/cm². Elasticity modulus of cured composition was 4500 kp/cm².

EXAMPLE 18

An adhesive composition was prepared using 60 g of ethyl-α-cyan acrylate, 20 g of n-butyl-α-cyan acrylate and 20 g of 1,1,5-trihydrooctafluoro-n-amyl methacrylate. The adhesive composition was prepared as described in Example 2. The adhesive composition was tested as described in Example 1. Shear strength was 160 kp/cm². Elasticity modulus of cured adhesive composition was 6000 kp/cm².

EXAMPLE 19

An adhesive composition was prepared using 50 g of ethyl-α-cyan acrylate, 20 g of n-heptyl-α-cyan acrylate and 30 g of 1,1,7-trihydrododecafluoro-n-heptyl methacrylate. The adhesive composition was prepared as described in Example 2. The adhesive composition was tested as described in Example 1. Shear strength was 150 kp/cm². Elasticity modulus of cured adhesive composition was 3500 kp/cm².

EXAMPLE 20

An adhesive composition was prepared using 60 g of ethyl-α-cyan acrylate, 20 g of allyl-α-cyan acrylate containing 0.002 g of hydroquinone and 20 g of 1,1,7-trihydrododecafluoro-n-heptyl methacrylate. The preparation and testing of adhesive composition were conducted as described in Example 1. Shear strength was 140 kp/cm². Elasticity modulus of cured composition was 5000 kp/cm².

EXAMPLE 21

An adhesive composition was prepared using 70 g of methyl-α-cyan acrylate containing 0.001 g of hydroquinone and 30 g of 1,1,7-trihydrododecafluoro-n-heptyl acrylate. The preparation and testing of adhesive composition were conducted as described in Example 1. Shear strength was 190 kp/cm². Elasticity modulus of cured adhesive composition was 9000 kp/cm².

What is claimed is:

1. An adhesive composition containing monomeric -α-cyanacrylates selected from the group consisting of alkyl-α-cyanacrylates, wherein alkyl group contains from 1 to 7 carbon atoms, and allyl-α-cyanacrylate, as well as a modifying additive selected from the group of monomeric fluorinated acrylates consisting of fluorinated methacrylate and fluorinated acrylate of the general formula

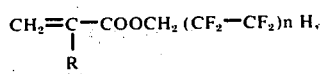

wherein $n=1-3$, R is H, CH$_3$, and

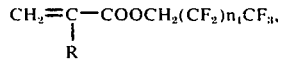

wherein $n_1$=1–2, and R has the above-mentioned significances, monomeric α-cyanacrylates being used in an amount of 70–90 w.% and the modifying additive in an amount of 10–30 w.%.

2. An adhesive composition according to claim 1, containing also an inhibitor of radical polymerization in an amount of 0.01–0.05% by weight of the adhesive composition.

3. An adhesive composition according to claim 2, wherein said inhibitor of radical polymerization comprises hydroquinone.

4. An adhesive composition according to claim 2, wherein said inhibitor of radical polymerization comprises methylhydroquinone.

UNITED STATES PATENT AND TRADEMARK OFFICE
CERTIFICATE OF CORRECTION

PATENT NO. : 4,009,044
DATED : February 22, 1977
INVENTOR(S) : KORSHAK ET AL

It is certified that error appears in the above-identified patent and that said Letters Patent are hereby corrected as shown below:

Please change the formula in the Abstract to read:

$$CH_2 = \underset{R}{\underset{|}{C}} - COOCH_2 \, (CF_2-CF_2)_n \cdot H$$

Please amend the next line after said formula to read:

--wherein n=1-3, R is H, $CH_3$, or $CH_2=\underset{R}{\underset{|}{C}}-COOCH_2$--

Column 3, amend formula as follows:

$$CH_2=\underset{R}{\underset{|}{C}}-COOCH_2(CF_2)n_1 \cdot CF_3$$

Signed and Sealed this

*Twentieth* Day of *June 1978*

[SEAL]

*Attest:*

RUTH C. MASON
*Attesting Officer*

DONALD W. BANNER
*Commissioner of Patents and Trademarks*